United States Patent [19]

Suzuki et al.

[11] Patent Number: 5,738,669
[45] Date of Patent: Apr. 14, 1998

[54] ABSORBENT ARTICLE

[75] Inventors: Mikio Suzuki, Utsunomiya; Ken Takeuchi, Haga-gun; Masashi Wada, Utsunomiya, all of Japan

[73] Assignee: Kao Corporation, Tokyo, Japan

[21] Appl. No.: 557,096

[22] PCT Filed: Mar. 31, 1995

[86] PCT No.: PCT/JP95/00622

§ 371 Date: Dec. 6, 1995

§ 102(e) Date: Dec. 6, 1995

[87] PCT Pub. No.: WO95/27516

PCT Pub. Date: Oct. 19, 1995

[30] Foreign Application Priority Data

Apr. 12, 1994 [JP] Japan ................... 6-073236
May 17, 1994 [JP] Japan ................... 6-102866

[51] Int. Cl.[6] ............................................. A61F 13/15
[52] U.S. Cl. .................................... 604/367; 604/389
[58] Field of Search ............................. 604/358, 367, 604/370, 372, 386, 389, 390; 428/270–272, 274

[56] References Cited

U.S. PATENT DOCUMENTS 4,526,577  7/1985  Schmidt, Jr. et al. .............. 604/372
4,822,350  4/1989  Ito et al. ........................... 604/370

FOREIGN PATENT DOCUMENTS 0105629      4/1984   European Pat. Off. .
0 192 965 A1 9/1986   European Pat. Off. ......... 604/358
0 196 654 A2 10/1986  European Pat. Off. ......... 604/358
0 307 116    3/1989   European Pat. Off. ......... 604/358
4-77591      3/1992   Japan .
4-84960      3/1992   Japan .

OTHER PUBLICATIONS

English Abstract of JP 4-77591.
English Abstract of JP 4-84960.

*Primary Examiner*—Robert A. Clarke
*Attorney, Agent, or Firm*—Birch, Stewart, Kolasch & Birch, LLP

[57] ABSTRACT

An absorbent article (1) having a moisture permeable sheet coated with an adhesive agent is characterized in that: the sheet comprises a porous sheet obtainable by preparing, a melt blended solution comprising, a crystalline polyolefin and a compound with which the polyolefin is miscible and in which the polyolefin will dissolve at or above the melting point of the polyolefin but which will phase separate below the melting point of the polyolefin, molding the solution into a sheet, and stretching the sheet at least in one direction to form micropores; and the sheet has a moisture permeability of 0.5 to 4 g/100 cm$^2$.h, a tensile load at 3% elongation in the transverse direction of 100 to 300 g/cm, a bulk softness of 55 g or less, a break strength of 250 g/cm or more, and a reduction in reflectance on the area coated with the adhesive agent of 20% or less.

15 Claims, 2 Drawing Sheets

FIG. 1(a)
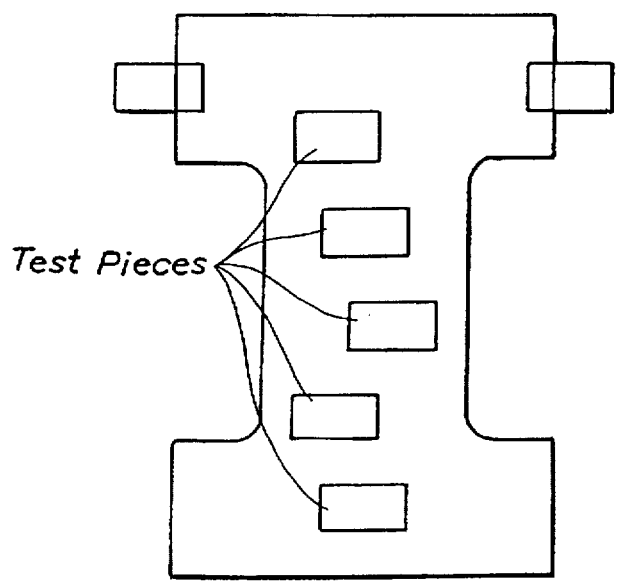
Test Pieces
FIG. 1(b)
FIG. 2(a)
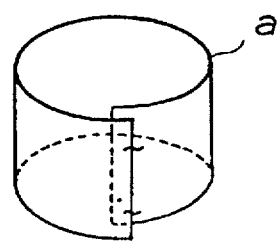
FIG. 2(b)
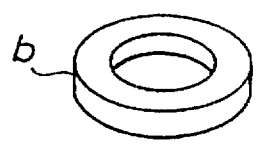
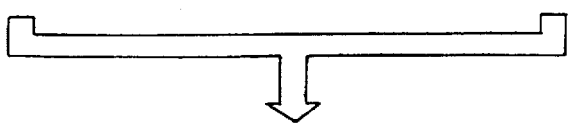
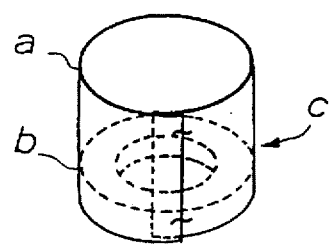
FIG. 2(c)

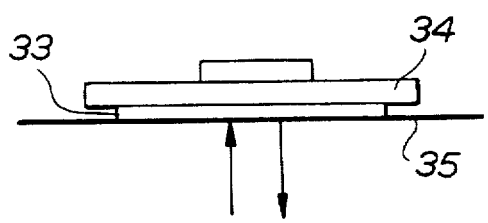
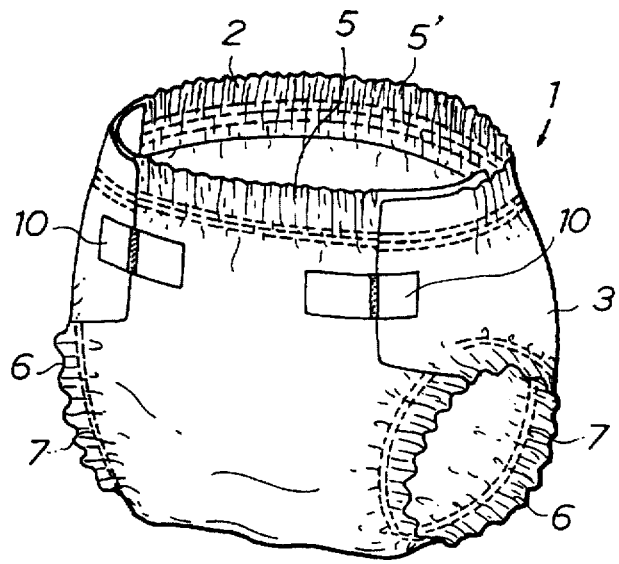
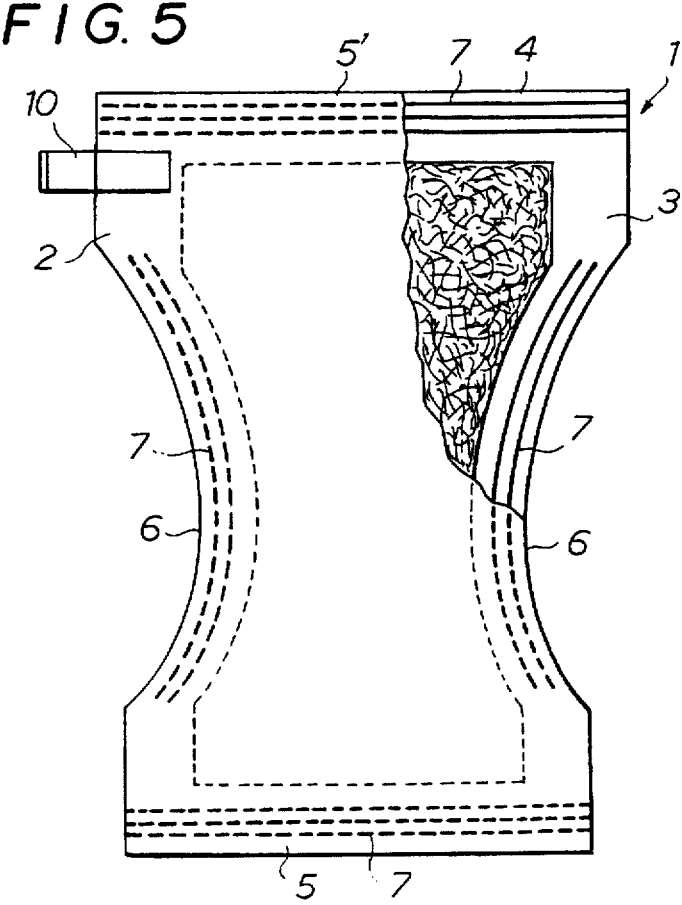

5,738,669

ABSORBENT ARTICLE

This application is a 371 application of PCT/JP/00.622 filed on Mar. 31, 1995.

TECHNICAL FIELD

This invention relates to absorbent articles using a moisture permeable sheet, such as disposable diapers. More particularly, it relates to an absorbent article which undergoes little bleeding of a softening agent used as a component of an adhesive agent and/or a compound with which a crystalline polyolefin is miscible and in which said crystalline polyolefin will dissolve at or above the melting point of said crystalline polyolefin but which will phase separate below the melting point of said crystalline polyolefin. The bleeding of the softening agent and/or the compound causes the adhesive agent coated area of the moisture permeable sheet to be transparent (this phenomenon will hereinafter be referred to as bleed-through).

BACKGROUND ART

Absorbent articles are generally fabricated from a liquid permeable sheet (topsheet), a liquid impermeable sheet (back sheet) and an absorbent member interposed the topsheet and the back sheet, the three elements being adhered together with an adhesive agent at prescribed potions of the three elements.

Among the absorbent articles, disposable diapers use a liquid impermeable sheet endowed with moisture permeability so as to prevent stuffiness and a diaper rash. On the other hand, adhesive agents predominantly used for adhesion of the liquid impermeable back sheet usually contains an increased amount of a softening agent in order to improve initial adhesion and coating properties.

However, when such an adhesive agent is applied to the moisture permeable sheet, the softening agent migrates into the sheet (bleed-through) causing various problems, such as stickiness on the surface of the moisture permeable sheet, adverse influences on performance characteristics of the absorbent articles such as diapers, blocking of the absorbent articles when stacked for storage, and change of adhesion characteristics of the adhesive agent with time due to the change in composition.

Further, the above-mentioned moisture permeable sheet contains a softener for manifestation of moisture permeability and softness. Application of the adhesive agent having an increased amount of the softening agent to such a moisture permeable sheet containing the softener leads to acceleration of the above-mentioned bleed-through.

In order to overcome these problems, Japanese Patent Application Laid-opens 4-77591 and 4-84960 propose adhesive agents applicable to the moisture permeable sheet.

The adhesive agent disclosed in the above-mentioned Japanese Patent Application Laid-open 4-77591 is a hot melt adhesive agent comprising, as main components, an α-olefin resin and a styrene-ethylene-propylene-styrene block copolymer and further containing a tackifier and a plasticizing oil. According to the above Laid-open application, when the adhesive agent is used for adhering a moisture permeable sheet and nonwoven fabric, no bleed-through of low-molecular weight components occurs, and the tack is lost to show no stickiness on cooling to solidify.

However, the above Laid-open application specifies neither moisture permeability of the moisture permeable sheet nor the bleeding properties on the area to which the adhesive agent has been applied. Another problem associated with this adhesive agent is that in using a moisture permeable sheet comprising a crystalline polyolefin and a softener, the softener contained in the sheet tends to migrate to make the sheet transparent.

The adhesive agent disclosed in the above-mentioned Japanese Patent Application Laid-open 4-84960 comprises a styrene block polymer, a tackifier, and a softening agent, in which the activation energy of the styrene segments and the rubber segments is specified. The above Laid-open application also refers to an absorbent article hardly suffering from bleed-through, which can be obtained by adhering a moisture permeable sheet having a specific moisture permeability with the above adhesive agent.

However, the above Laid-open application provides no specific range of formulation of the adhesive agent. The adhesive agent also involves the above-described disadvantage occurring in application to a moisture permeable sheet comprising a crystalline polyolefin and a softener.

DISCLOSURE OF THE INVENTION

Accordingly, an object of the present invention is to provide an absorbent article comprising a moisture permeable sheet which exhibits excellent moisture permeability, which is suitable to coating with an adhesive agent, and having high initial adhesion with the adhesive agent.

Another object of the present invention is to provide an absorbent article which undergoes little bleed-through of a softening agent contained in the adhesive agent or a softener contained in a moisture permeable sheet, and can therefore avoid various disadvantages resulting from the bleed-through of the softening agent or softener, such as stickiness on the surface of the moisture permeable sheet, impairment of appearance, and in various performance characteristics.

Still another object of the present invention is to provide an absorbent article which undergoes little blocking of the absorbent articles such as diapers when stacked for storage, and deterioration of adhesion due to changes of the composition of the adhesive agent with time.

In order to solve the above-mentioned problems, the present inventors have conducted extensive investigations and, as a result, found that the above object of the present invention can be accomplished by an absorbent article having a moisture permeable sheet which is specified by its main components, moisture permeability, and reduction in reflectance on the area coated with an adhesive agent.

The present invention has been completed based on this finding. The present invention provides an absorbent article having a moisture (water vapor) permeable sheet coated with an adhesive agent, characterized in that the moisture permeable sheet is a porous sheet obtainable by preparing, by melt blending, a melt blended solution comprising, as main components, a crystalline polyolefin and a compound with which said crystalline polyolefin is miscible and in which said crystalline polyolefin will dissolve at or above the melting point of said crystalline polyolefin but which will phase separate below the melting point of said crystalline polyolefin, molding said melt blended solution into a sheet, and stretching said sheet at least in one direction to form micropores; and said moisture permeable sheet has a moisture permeability falling within the range of 0.5 to 4 g/100 cm$^2$.h, a tensile load at 3% elongation in the transverse direction of said sheet falling within the range of 100 to 300 g/cm, a bulk softness of 55 g or less, a break strength of 250 g/cm or more, and a reduction in reflectance on the area coated with said adhesive agent, after preserved at 50° C. for 1 day, of 20% or less.

BRIEF DESCRIPTION OF THE DRAWINGS

FIGS. 1(a) and 1(b) schematically show the sampling positions and the dimension of test pieces for measurement of tensile load at 3% elongation;

FIGS. 2(a), 2(b) and 2(c) schematically show the manner of preparing a test piece for measurement of bulk softness;

FIG. 3 illustrates the principle of measurement of bleed-through;

FIG. 4 is a perspective view of a disposable diaper, a preferred embodiment of the present invention, seen from the front side (stomach side); and FIG. 5 is a view in which the disposable diaper of FIG. 4 is laid flat.

BEST MODE FOR CARRYING OUT THE INVENTION

The absorbent article according to the present invention will be described below in detail.

The moisture permeable sheet used in the absorbent article of the present invention comprises specific components and exhibits a specific moisture permeability, a specific tensile load at 3% elongation in the transverse direction, a specific bulk softness, a specific break strength, and a specific reduction in reflectance.

The specific components which can be used as the main components are a crystalline polyolefin and a compound with which said crystalline polyolefin is miscible and in which said crystalline polyolefin will dissolve at or above the melting point of said crystalline polyolefin but which will phase separate below the melting point of said crystalline polyolefin (hereinafter referred to as softener A).

The moisture permeable sheet mainly comprising the crystalline polyolefin and the softener A and having a moisture permeability falling within a specific range hereinafter described has sufficient strength while retaining moisture permeability. When used, for example, as a back sheet of a disposable diaper, the moisture permeable sheet makes the fastening tape directly attached thereon or detached therefrom.

The moisture permeable sheet may consist of the above-mentioned main components. However, it may further contain additives employed in general moisture permeable sheets. This being the case, the main components are preferably present in a proportion from 80 to 100% by weight based on the moisture permeable sheet.

The crystalline polyolefin which can be used in the present invention includes a polypropylene, specifically a propylene homopolymer, a propylene-other olefin copolymer, a blend of a polypropylene and a propylene-other olefin copolymer, a blend of a polypropylene and a polyethylene, and a blend of a propylene-other olefin copolymer and a polyethylene.

The crystalline propylene polymers preferably include those having an isotactic pendant content (P) and a melt flow rate (MFR) satisfying the relationship: $1.00 \geq P \geq 0.015 \log MFR + 0.955$.

The term "isotactic pendant content (P)" as used herein denotes an indication for crystalline properties of a polypropylene. The MFR is preferably in the range of from 0.03 to 2.0 g/10 min.

The softener A is not particularly limited as far as it is a compound with which said crystalline polyolefin is miscible and in which said crystalline polyolefin will dissolve at or above the melting point of said crystalline polyolefin but which will phase separate below the melting point of said crystalline polyolefin. Examples of the suitable softeners A are mineral oils, synthetic lubricating oils, dioctyl phthalate, diethyl phthalate, triethylene glycol, dibutyl phthalate, and other esters between an alkyl alcohol and a polybasic carboxylic acid, e.g., phthalic acid, trimellitic acid, pyromellitic acid and/or a fatty acid.

The moisture permeable sheet of the present invention has a moisture permeability of from 0.5 to 4 g/100 cm².h, preferably from 1.0 to 2.5 g/100 cm².h. The moisture permeability assures prevention of stuffiness while maintaining leakproofness.

The moisture permeable sheet has a tensile load at 3% elongation of from 100 to 300 g/cm, preferably from 100 to 200 g/cm, in the transverse direction. If the tensile load is less than 100 g/cm, when a tensile load is imposed on a fastening tape adhered to the back sheet, the back sheet is too stretchable for the fastening tape to follow the stretch of the back sheet, and the fastening tape would be detached or broken at the stretched portion. If the tensile load exceeds 300 g/cm, the back sheet does not stretch sufficiently for following the wearer's movement, and the diaper gives an unpleasant feeling. The transverse direction as used herein is a direction to which the longitudinal direction of the absorbent article is perpendicular when the moisture permeable sheet is assembled into the absorbent article. The transverse direction of the moisture permeable sheet may be the direction same as or different from the cross-sectional direction (perpendicular to the machine direction) during the manufacture thereof.

The moisture permeable sheet of the present invention has a bulk softness of 55 g or less, preferably 45 g or less, still preferably from 30 to 40 g. If the bulk softness exceeds 55 g, the back sheet has poor softness, and the diaper feels stiff and uncomfortable.

The moisture permeable sheet of the present invention has a break strength of 250 g/cm or greater, preferably from 300 to 1000 g/cm. If the break strength is less than 250 g/cm, the back sheet would be broken in detachment of a fastening tape.

The above physical properties are measured in the manner described below.

1. Tensile load of back sheet at 3% elongation (1) Measuring apparatus

Tensilon universal testing apparatus, tensile test mode (supplied by Orientec Co., Ltd.)

(2) Test Pieces

As illustrated in FIG. 1(a), test pieces are taken from five positions of the diaper. (At this time, in cases where adhesive agents or absorbent papers cling to the back sheet, they should be removed by an organic solvent such as toluene to such an extent that the back sheet may not be affected adversely.) As illustrated in FIG. 1(b), the size of each test piece is 10 mm×(25 mm+50 mm+25 mm).

(3) Measurement conditions i) Measuring environment: Temperature 20° C., Humidity 65% RH ii) Tensile conditions: Distance between chucks; 50 mm, Rate of elongation; 300 mm/min (4) Measurement results The tensile strength of each test piece at 3% elongation (when the distance between chucks of 50 mm is increased to 51.5 mm) is measured. The mean value of the values measured for five test pieces is calculated.

2. Bulk softness of back sheet (1) Measuring apparatus

Tensilon universal testing apparatus, compression test mode (supplied by Orientec Co., Ltd.)

(2) Test Pieces i) Test pieces are taken from the same positions as in the sampling for the measurement of the tensile load of the back sheet at 3% elongation in item 1 (The test pieces were taken in the transverse direction of the moisture permeable sheet.). The size of the test pieces is 30×150 mm.

ii) Specimen: As illustrated in FIG. 2(a), each test piece is formed into a cylinder a having a diameter of 45 mm and a height of 30 mm in such a manner that the outer side of the cylinder corresponds to the outer surface of the back sheet. The upper and lower ends of the overlapped portion are fixed by using a stapler. Thereafter, a ring b made of polyvinyl chloride shown in FIG. 2(b) is fitted to the lower portion of the cylinder a. In this manner, a specimen c shown in FIG. 2(c) is obtained.

(3) Measurement conditions i) Measuring environment: Temperature 20° C., Humidity 65% RH ii) Compressing conditions: Rate of compression; 10 mm/min (Compression is conducted in the direction along the height of the cylinder, which corresponds to the transverse direction of the moisture permeable sheet.)

(4) Measurement results

The maximum strength of each test piece is measured when the test piece is compressed by 20 mm. The mean value of the values measured for five test pieces is calculated and taken as the bulk softness.

3. Break strength of back sheet

The test is carried out in the same manner as that in the measurement of the tensile load of the back sheet at 3% elongation in item 1. The load at the time of breakage is measured and taken as the break strength (The break strength is measured in the transverse direction of the permeable sheet.).

The moisture permeable sheet of the present invention has a reduction in reflectance of 20% or less, preferably from 0 to 15%, on the area coated with an adhesive agent, after preserved at 50° C. for 1 day. While the method of measuring the reflectance will be explained later, the term "reduction in reflectance" as used herein means a percent reduction in reflectance calculated from equation:

Reduction in reflectance (%)=100−[(reflectance after preserved at 50° C. for 1 day)/(initial reflectance)]×100

If an adhesive agent-coated area of the moisture permeable sheet shows a reduction in reflectance exceeding 20%, this indicates that the area has obviously been made transparent due to bleed-through of the adhesive agent, suffering from deterioration of appearance, stickiness to touch, and reduction in adhesion.

The moisture permeable sheet used in the present invention is a porous sheet obtainable by the following manner using the above-mentioned main components.

The crystalline polyolefin and the softener A are melt-blended to form a melt blended solution. The melt blended solution is molded into a sheet, and the resulting sheet is stretched at least one direction to form micropores.

The mixing ratio of the crystalline polyolefin and the softener A is preferably from 30 to 80 by weight of crystalline polyolefin and from 20 to 70 by weight of the softener A.

The adhesive agent which can be used for adhesion of the moisture permeable sheet preferably includes those comprising a base polymer, a tackifier which is solid at room temperature, and a component which is liquid at room temperature (hereinafter referred to as a softening agent).

Suitable softening agents include those having a softening point of 10° C. or lower and having an average molecular weight of 200 to 700, including process oil, mineral oil, various plasticizers, polybutene, and liquid adhesive resins. Specific examples of these softening agents include paraffin oils, e.g., "Shellflex" (a product of Shell Chemical), "PW90" (a product of Idemitsu Petrochemical Co., Ltd.), and ester oils, e.g., tetraoctyl pyromellitate, didodecyl phthalate, and trioctyl trimellitate.

The content of the softening agent in the adhesive agent is preferably 20% by weight or lower, preferably from 0 up to 14% by weight. If the content of the softening agent exceeds 20% by weight, bleed-through tends to become conspicuous.

Examples of suitable base polymers of the adhesive agent include natural rubber; isoprene rubber; styrene rubbers, e.g., styrene-butadiene rubber, a styrene-butadiene-styrene block copolymer (SBS), a styrene-isoprene-styrene block copolymer (SIS), a styrene-ethylene-butylene-styrene block copolymer (SEBS), and a styrene-ethylene-propylene-styrene block copolymer (SEPS); and olefin polymers, e.g., amorphous poly-α-olefins (APAO) and an ethylene-vinyl acetate copolymer (EVA).

The tackifiers which are solid at room temperature include C5 petroleum resins, C9 petroleum resins, dicylopentadiene petroleum resins, rosin petroleum resins, polyterpene resins, and terpene phenol resins, specifically hydrogenated terpene resins such as "Clearon" (a product of Yasuhara Kagaku K.K.) and hydrogenated aromatic petroleum resins such as "Alcon" (a product of Arakawa Chemical K.K.).

The amount of the tackifier to be used should be selected appropriately depending on the content of the softening agent. That is, where the content of the softening agent is 20% by weight or less based on the total adhesive agent, the amount of the tackifier is not limited and usually selected from the range of from 30 to 70% by weight based on the total adhesive agent. Alternatively, it is possible to use the softening agent in a proportion of more than 20% by weight up to 30% by weight based on the total adhesive agent. In this case, the tackifier is used in an amount of 30% by weight or less, preferably 10% by weight or less, still preferably from 5 to 10% by weight, based on the total adhesive agent.

In case where the content of the tackifier and the softening agent exceed 10% by weight and 20% weight, respectively, the adhesive agent tends to make the moisture permeable sheet transparent and to reduce its adhesive strength.

While adhesive agents satisfying the above-mentioned conditions of formulation and components are satisfactorily usable, those having a melt viscosity at 180° C. of 10000 cps or less, particularly from 1000 to 8000 cps are preferred. Adhesive agents whose melt viscosity exceeds 10000 cps tend to have reduced coating properties, causing unevenness of coating or drips.

The adhesive agent preferably contains 5% by weight or less, preferably from 0.5 to 3% by weight, of inorganic fillers based on the total adhesive agent thereby reducing the reduction in reflectance by about 5%. That is, addition of inorganic fillers to the adhesive agent which causes a reduction in reflectance of, for example, 25% reduces the reduction to 20%. However, the adhesive agent having an inorganic filler content of more than 5% becomes whiter than the moisture permeable sheet and gives a distinguishable pattern of application when applied to the moisture permeable sheet, making the appearance poor. Moreover, such an adhesive agent sometimes has reduced adhesive strength.

Suitable inorganic fillers include titanium oxide, zinc white, silica, calcium carbonate, aluminum hydroxide, barium sulfate, starch, and talc.

The adhesive agents satisfying the above-described preferred conditions of formulation and components are satisfactorily applicable to the moisture permeable sheet mainly comprising a polypropylene and the softener A. They are especially preferred in the present invention; for they suffer from no reduction in adhesive strength due to bleed-through of the softener A and does not make the moisture permeable sheet transparent.

The adhesive agent may further contain an antioxidant, such as "Irganox 1010" (a product of Ciba-Geigy Ltd.), "Irganox 1076" (a product of Ciba-Geigy Ltd.) or "Sumilizer GM" (a product of Sumitomo Chemical Co., Ltd.). The antioxidant is preferably added in an amount of 1 to 3 parts by weight per 100 parts by weight of the base polymer.

The bleed-through can be evaluated by measuring the degree of transparency of the adhesive agent-coated area of the moisture permeable sheet after preserved at 50° C. for 1 day. If the adhesive agent applied to the moisture permeable sheet bleeds during storage, the softener A and/or the softening agent bleed out (migrate) to the surface of the moisture permeable sheet, and the sheet becomes transparent as if frosted glass becomes light transmitting upon being wetted with water, having an object on the other side seen through.

The degree of transparency can be determined quantitatively, for example, as in a manner shown in FIG. 3. The moisture permeable sheet 33 coated with the adhesive agent is placed on a black plate 34, and a transparent glass plate 35 is put thereon. The top surface of the sheet 33 is irradiated with blue light having a wavelength of 459 nm, and the reflectance is measured.

According to this measuring method, if the degree of bleed-through is high, that is the amount of the softener A and/or the softening agent which bleed out (migrate) to the surface of the sheet 33 is large, the blue incident light is transmitted through the sheet 33 and absorbed into the black plate 34 so that the reflectance of the sheet 33 is reduced. If the degree of bleed-through is low, that is the amount of the softener A and/or the softening agent which bleed out (migrate) to the surface of the sheets is small, the blue incident light hardly passes through the sheet 33 and hardly reaches the black plate 34 and is reflected on the surface of the sheet 33 at a high reflectance.

In other words, if the reflectance measured after preserved at 50° C. for 1 day is considerably lower than the initial reflectance, this indicates that considerable bleed-through has occurred during the storage.

The absorbent articles according to the present invention preferably include disposable diapers and sanitary napkins, which comprises a liquid permeable topsheet, an absorbent member capable of absorbing and retaining a body fluid, and a liquid impermeable back sheet, the back sheet comprising the moisture permeable sheet of the present invention and being adhered to the other elements with the above-mentioned adhesive agent. Conventional techniques or knowledge with respect to materials of the topsheet and the absorbent member, the structure of each element, the whole structure, and the like can be applied to the absorbent articles of the present invention with no particular limitation.

A disposable diaper which is a preferred embodiment of the present invention is illustrated below by referring to FIGS. 4 and 5.

A diaper 1 as shown in FIGS. 4 and 5, which is a preferred embodiment of the absorbent article of the present invention, comprises a topsheet 2 comprising a liquid permeable sheet, a liquid impermeable back sheet comprising the above-described moisture permeable sheet, and an absorbent member 4 interposed between the topsheet 2 and the back sheet 3. These three elements are adhered together with the adhesive agent applied to prescribed portions, specifically almost all the contact area between the topsheet 2 and the absorbent member 4 and almost all the contact area between the back sheet 3 and the absorbent member 4. A reinforcement tape (sometimes referred to as a target tape) usually used in disposable diapers is not provided.

In greater detail, as shown in FIGS. 4 and 5, the absorbent member 4 has a hourglass shape with its middle part corresponding to the crotch narrowed. The topsheet 2 and the back sheet 3 also have their middle part narrowed in agreement with the shape of the absorbent member 4. The absorbent member 4 is supported by the topsheet 2 and the back sheet 3. Elastic stretching members 7 are provided at a front waist part 5, a rear waist part 5', and leg parts 6 so that the diaper 1 may fit the body of a wearer.

The materials and structures of the topsheet 2, the absorbent member 4, and the whole structure of the diaper are the same as in conventional disposable diapers.

The disposable diaper 1 has fastening tapes 10. A peel strength required to peel the fastening tape 10 from the back sheet 3 (the moisture permeable sheet of the present invention) at 180° is 400 g/cm or less, the peel strength at 180° being measured after the fastening tape 10 and the back sheet 3 are adhered together and allowed to stand at 40° C. and 80% RH for 24 hours, and a time required until the fastening tape 10 and the back sheet 3 are peeled from each other under a load of 500 g of 10 minutes or longer. Therefore, it may be attached onto and detached from any desired position on the surface side of the back sheet 3.

The present invention will now be illustrated in greater detail with reference to Examples, but it should be understood that the present invention is not deemed to be limited thereto.

EXAMPLES 1 TO 9

The base polymer, tackifier, softening agent, inorganic filler, and antioxidant shown in Table 1 below were compounded according to the formulation shown in Table 1 and melt-blended at about 180° C. for 40 minutes to obtain an adhesive agent. The melt viscosity of the adhesive agent was measured by the method described below. The results obtained are shown in Table 1.

Measurement of Melt Viscosity:

The adhesive agent was kept at 180° C., and the melt viscosity was measured with a Brookfield viscometer, manufactured by Tokyo Keiki K.K.

The adhesive agent kept at 180° C. was applied to the entire surface of the release paper to a thickness of 30±5µ by hot-melt coating, and the adhesive layer was transferred onto a moisture permeable sheet comprising a polypropylene, a propylene-ethylene block copolymer, and a softener and having a moisture permeability of 1.4 g/100 cm$^2$.h. The reflectance of the sheet was measured immediately after the transfer coating and after the adhesive-coated sheet was allowed to stand at 50° C. for 1 day to obtain a reduction in reflectance. Further, adhesion performance of the adhesive agent was evaluated in accordance with the testing method described below. The results obtained are shown in Table 2.

The moisture permeable sheet used here was prepared as follows. Pellets of a resin composition comprising a polypropylene, a softener and, if desired, various additives were melt-blended in a twin-screw extruder and blown into a film using an air cooling type inflation molding machine. The blown film was 1.5-fold stretched in the machine direction by means of a roll stretching machine.

The polypropylene used was a dry blend of 70 parts by weight of a polypropylene WT6048 (a product of Chisso Sekiyu Kagaku K.K.) and 30 parts by weight of a propylene-ethylene block copolymer WT6052 (a product of Chisso Sekiyu Kagaku K.K.). The softener used was liquid paraffin PW90 (a product of Idemitsu Petrochemical Co., Ltd.). The weight ratio of the polypropylene to the softener was 7:3. The resulting moisture permeable sheet had a thickness of about 40μ. The moisture permeable sheet has a tensile load of at 3% elongation in the transverse direction of 144 g/cm, a bulk softness of 15 g, and a break strength of 607 g/cm.

Evaluation of Adhesion Performance:

The adhesive agent at 180° C. was applied to the moisture permeable sheet by means of a spiral spray to a coverage of 15 g/m² and a coating width of 13 mm. Nonwoven fabric commonly used as a topsheet of an absorbent article such as a disposable diaper was bonded thereto with an open time (time required from the moment the adhesive agent is applied until the nonwoven fabric is bonded) of 2 seconds.

After the bonded laminate was allowed to stand at 20° C. and 50° C. for 1 day, respectively, the moisture permeable sheet and the nonwoven fabric were peeled apart. The adhesion was rated "good" when the nonwoven fabric is broken, or "poor" when they were peeled from each other.

EXAMPLES 10 TO 12

A moisture permeable sheet having a thickness of about 40μ, a moisture permeability of 2.1 g/100 cm².h, a tensile load at 3% elongation in the transverse direction of 149 g/cm and a bulk softness of 17 g and break strength of 572 g/cm was prepared in the same manner as in Example 1 using a composition comprising 66 parts by weight of a polypropylene B200 (a product of Mitsui Petrochemical Industries, Ltd.), 4 parts by weight of a 2 wt % nucleating agent master batch EC-1 (a product of EC Kagaku K.K.), and 30 parts by weight of liquid paraffin PW90 (a product of Idemitsu Petrochemical Co., Ltd.). Each of the adhesive agents used in Examples 1, 3 and 8 was applied to the moisture permeable sheet in the same manner as in Example 1 to measure a reduction in reflectance and evaluate adhesion performance. The results obtained are shown in Table 3 below.

TABLE 1

| Composition (part by weight) | Example | | | | | | | | |
|---|---|---|---|---|---|---|---|---|---|
| | 1 | 2 | 3 | 4 | 5 | 6 | 7 | 8 | 9 |
| Base Polymer  SEBS | 30 | 30 | 30 | 30 | 30 | 30 | 30 | 65 | |
| APAO | | | | | | | | | 55 |
| Tackifier | | | | | | | | | |
| Hydrogenated Terpene Resin*¹ | 60 | 60 | 60 | 60 | 60 | 60 | 60 | | 35 |
| Hydrogenated Aromatic Petroleum Resin*² | | | | | | | | 5 | |
| Softening agent | | | | | | | | | |
| Paraffin Oil*³ | 5 | 10 | 14 | 10 | | | | 30 | 10 |
| Ester Oil*⁴ | | | | | 5 | 10 | 14 | | |
| Inorganic Filler | | | | | | | | | |
| Titanium Oxide | | | | 1.5 | | | | | 1.5 |
| Antioxidant | | | | | | | | | |
| Hindered Phenol*⁵ | 0.3 | 0.3 | 0.3 | 0.3 | | | | | |
| Melt Viscosity (cps, 180° C.) | 3300 | 1700 | 1200 | 1700 | 3500 | 2000 | 1500 | 2200 | 3500 |

Note: *¹ to *⁵ in Table 1 denotes the following.
*¹Clearon P105 (a product of Yasuhara Kagaku K.K.)
*²Alcon 100 (a product of Arakawa Kagaku K.K.)
*³PW90 (a product of Idemitsu Petrochemical Co., Ltd.)
*⁴Adecasizer UL-80 (a product of Asahi Denka Kogyo K.K.)
*⁵Irganox 1010 (a product of Ciba-Geigy Ltd.)

TABLE 2

| | Example | | | | | | | | |
|---|---|---|---|---|---|---|---|---|---|
| | 1 | 2 | 3 | 4 | 5 | 6 | 7 | 8 | 9 |
| Reduction in Reflectance (%) | 1 | 3 | 0 | 5 | 3 | 4 | 2 | 0 | 0 |
| Adhesion Performance  20° C. | good | good | good | good | good | good | good | good | good |
| 50° C. | good | good | good | good | good | good | good | good | good |

TABLE 3

|  |  | Example | | |
|---|---|---|---|---|
|  |  | 10 | 11 | 12 |
| Reduction in Reflectance (%) | | 2 | 14 | 1 |
| Adhesion | 20° C. | good | good | good |
| Performance | 5° C. | good | good | good |

INDUSTRIAL APPLICABILITY

The absorbent article according to the present invention exhibits excellent moisture permeability, suitability to coating with an adhesive agent and high initial adhesion with the adhesive agent, and undergoes little bleed-through of a softening agent present in the adhesive agent or a softener present in a moisture permeable sheet and can therefore avoid various disadvantages resulting from the bleed-through of the softening agent and/or softener, such as stickiness on the surface of the moisture permeable sheet, impairment of appearance, deterioration in various performance characteristics, blocking of the stacked absorbent articles during storage, and deterioration of adhesion due to change of the composition of the adhesive agent with time.

The invention has been described by way of the preferred embodiments thereof. The above-described embodiments are, therefore, intended to be merely exemplanary, and many other variations and modifications of the invention are included within the scope of the invention.

We claim:

1. A moisture permeable sheet comprising a porous sheet obtained by melt blending a melt blended solution comprising, as main components, a crystalline polyolefin and a compound with which said crystalline polyolefin is miscible and in which said crystalline polyolefin will dissolve at or above the melting point of said crystalline polyolefin but which will phase separate below the melting point of said crystalline polyolefin, molding said melt blended solution into a sheet, and stretching said sheet at least in one direction to form micropores;

said moisture permeable sheet having a moisture permeability falling within the range of 0.5 to 4 g/100 cm².h, a tensile load at 3% elongation in the transverse direction of said sheet falling within the range of 100 to 300 g/cm, a bulk softness of 55 g or less, a break strength of 250 g/cm or more, and a reduction in reflectance on the area coated with an adhesive agent, after preserved at 50° C. for 1 day, of 20% or less.

2. A disposable diaper comprising a liquid permeable topsheet, a liquid impermeable back sheet comprising a moisture permeable sheet comprising a porous sheet obtained by melt blending a melt blended solution comprising, as main components, a crystalline polyolefin and a compound with which said crystalline polyolefin is miscible and in which said crystalline polyolefin will dissolve at or above the melting point of said crystalline polyolefin but which will phase separate below the melting point of said crystalline polyolefin, molding said melt blended solution into a sheet, and stretching said sheet at least in one direction to form micropores;

said moisture permeable sheet having a moisture permeability falling within the range of 0.5 to 4 g/100 cm².h, a tensile load at 3% elongation in the transverse direction of said sheet falling within the range of 100 to 300 g/cm, a bulk softness of 55 g or less, a break strength of 250 g/cm or more, and a reduction in reflectance on the area coated with an adhesive agent, after preserved at 50° C. for 1 day, of 20% or less, and an absorbent member interposed between said topsheet and said back sheet, said topsheet, said back sheet and said absorbent member being adhered together with an adhesive agent at prescribed portions of said three elements, and the disposable diaper has a fastening tape attachable onto and detachable from any portion of said back sheet.

3. The absorbent article as claimed in claim 2, wherein said crystalline polyolefin is a polypropylene.

4. The absorbent article as claimed in claim 3, wherein said polypropylene is a propylene homopolymer, a propylene-other olefin copolymer, a blend of a polypropylene and a propylene-other olefin copolymer, a blend of a polypropylene and a polyethylene, or a blend of a propylene-other olefin copolymer and a polyethylene.

5. The absorbent article as claimed in claim 2, wherein said adhesive agent contains 20% by weight or less of a component which is liquid at room temperature and 30% to 70% by weight of a tackifier which is solid at room temperature.

6. The absorbent article as claimed in claim 2, wherein said adhesive agent contains more than 20 up to 30% by weight of a component which is liquid at room temperature and 10% by weight or less of a tackifier which is solid at room temperature.

7. The absorbent article as claimed in claim 2, wherein said adhesive agent has a melt viscosity at 180° C. of 10000 cps or less.

8. The absorbent article as claimed in claim 2, wherein said adhesive agent contains 5% by weight or less of an inorganic filler.

9. A sanitary napkin comprising a liquid permeable topsheet, a liquid impermeable back sheet comprising a moisture permeable sheet comprising a porous sheet obtained by melt blending a melt blended solution comprising, as main components, a crystalline polyolefin and a compound with which said crystalline polyolefin is miscible and in which said crystalline polyolefin will dissolve at or above the melting point of said crystalline polyolefin but which will phase separate below the melting point of said crystalline polyolefin, molding said melt blended solution into a sheet, and stretching said sheet at least in one direction to form micropores;

said moisture permeable sheet having a moisture permeability falling within the range of 0.5 to 4 g/100 cm².h, a tensile load at 3% elongation in the transverse direction of said sheet falling within the range of 100 to 300 g/cm, a bulk softness of 55 g or less, a break strength of 250 g/cm or more, and a reduction in reflectance on the area coated with an adhesive agent, after preserved at 50° C. for 1 day, of 20% or less, and an absorbent member interposed between said topsheet and said back sheet, said topsheet, said back sheet and said absorbent member being adhered together with an adhesive agent at prescribed portions of said three elements, and the disposable diaper has a fastening tape attachable onto and detachable from any portion of said back sheet.

10. The sanitary napkin as claimed in claim 9, wherein said crystalline polyolefin is a polypropylene.

11. The sanitary napkin as claimed in claim 10, wherein said polypropylene is a propylene homopolymer, a propylene-other olefin copolymer, a blend of a polypropylene and a propylene-other olefin copolymer, a blend of a polypropylene and a polyethylene, or a blend of a propylene-other olefin copolymer and a polyethylene.

12. The sanitary napkin as claimed in claim 9, wherein said adhesive agent contains 20% by weight or less of a component which is liquid at room temperature and 30% to 70% by weight of a tackifier which is solid at room temperature.

13. The sanitary napkin as claimed in claim 9, wherein said adhesive agent contains more than 20 up to 30% by weight of a component which is liquid at room temperature and 10% by weight or less of a tackifier which is solid at room temperature.

14. The sanitary napkin as claimed in claim 9, wherein said adhesive agent has a melt viscosity at 180° C. of 10000 cps or less.

15. The sanitary napkin as claimed in claim 9, wherein said adhesive agent contains 5% by weight or less of an inorganic filler.

* * * * *